(12) United States Patent
Jelovac et al.

(10) Patent No.: US 9,795,985 B2
(45) Date of Patent: Oct. 24, 2017

(54) DISPENSING DEVICE FOR DENTAL MATERIAL

(71) Applicant: 3M INNOVATIVE PROPERTIES COMPANY, St. Paul, MN (US)

(72) Inventors: Emir Jelovac, München (DE); Jens Gramann, Gräfelfing (DE); Korbinian Schepke-Gerlach, Gauting (DE)

(*) Notice: Subject to any disclaimer, the term of this patent is extended or adjusted under 35 U.S.C. 154(b) by 194 days.

(21) Appl. No.: 14/379,959

(22) PCT Filed: Mar. 8, 2013

(86) PCT No.: PCT/US2013/029742
§ 371 (c)(1),
(2) Date: Aug. 20, 2014

(87) PCT Pub. No.: WO2013/134580
PCT Pub. Date: Sep. 12, 2013

(65) Prior Publication Data
US 2016/0023235 A1 Jan. 28, 2016

(30) Foreign Application Priority Data
Mar. 9, 2012 (EP) .................... 12158727

(51) Int. Cl.
*B05C 17/005* (2006.01)
*A61C 5/60* (2017.01)
(Continued)

(52) U.S. Cl.
CPC ............. *B05C 17/005* (2013.01); *A61C 5/60* (2017.02); *A61C 5/62* (2017.02); *B05C 17/01* (2013.01);
(Continued)

(58) Field of Classification Search
CPC .......... A61C 19/005; A61C 5/60; A61C 5/62; B65D 88/54; B65D 81/3283;
(Continued)

(56) References Cited

U.S. PATENT DOCUMENTS 4,583,934 A    4/1986 Hata
4,615,469 A *  10/1986 Kishi .................. B05C 17/0103
                                                      222/327

(Continued)

FOREIGN PATENT DOCUMENTS

EP    1700639    9/2006
EP    2324792    5/2011

OTHER PUBLICATIONS

International Search Report for PCT International Application No. PCT/US2013/029742, mailed on Jun. 27, 2013, 4pgs.

(Continued)

*Primary Examiner* — Patrick M Buechner
*Assistant Examiner* — Andrew P Bainbridge

(57) ABSTRACT

A dispensing device for dental material, which includes a planetary gear drive with at least three planet gears in engagement with an annulus gear. The annulus gear is radial float-mounted relative to the planet gears. A radial force applied on the annulus gear urges the annulus gear into an off-center relationship with respect to an imaginary circle on which the planet gears are arranged.

3 Claims, 3 Drawing Sheets

(51) Int. Cl.
*A61C 5/62* (2017.01)
*F16H 1/28* (2006.01)
*A61C 19/00* (2006.01)
*B65D 81/32* (2006.01)
*F16H 1/16* (2006.01)
*F16H 1/48* (2006.01)
*B01F 13/00* (2006.01)
*B05C 17/01* (2006.01)
*B65D 88/54* (2006.01)

(52) U.S. Cl.
CPC ........ *B05C 17/0103* (2013.01); *A61C 19/005* (2013.01); *B01F 13/002* (2013.01); *B01F 13/0018* (2013.01); *B01F 13/0027* (2013.01); *B05C 17/00553* (2013.01); *B05C 17/00559* (2013.01); *B05C 17/0116* (2013.01); *B65D 81/3227* (2013.01); *B65D 81/3283* (2013.01); *B65D 81/3288* (2013.01); *B65D 88/54* (2013.01); *F16H 1/16* (2013.01); *F16H 1/163* (2013.01); *F16H 1/166* (2013.01); *F16H 1/2809* (2013.01); *F16H 1/2818* (2013.01); *F16H 1/2827* (2013.01); *F16H 1/2836* (2013.01); *F16H 1/48* (2013.01)

(58) Field of Classification Search
CPC ............ B65D 81/3288; B65D 81/3227; B05C 17/0103; B05C 17/005; B05C 17/01; B05C 17/0116; B05C 17/00553; B05C 17/00559; B05B 11/0078; B05B 11/0081; B05B 11/02; B01F 13/002; B01F 13/0016; B01F 13/0018; B01F 2215/0027; B01F 2215/0039; B01F 13/0027; B01F 13/0039; F16H 1/16; F16H 1/163; F16H 1/166; F16H 1/2809; F16H 1/2818; F16H 1/2827; F16H 1/2836; F16H 1/48; F16H 2001/2872
USPC ... 222/145.1, 145.5–145.6, 63, 92–107, 129, 222/333, 1, 390–391; 475/331
See application file for complete search history.

(56) References Cited

U.S. PATENT DOCUMENTS

| | | | | |
|---|---|---|---|---|
| 5,269,733 | A * | 12/1993 | Anthony, III | B25B 21/026 173/171 |
| 5,853,346 | A * | 12/1998 | Gaffney | A61G 5/1054 475/1 |
| 5,909,830 | A * | 6/1999 | Bates | B05C 17/0103 222/327 |
| 6,315,164 | B1 * | 11/2001 | Muhlbauer | A61C 5/064 222/325 |
| 6,745,921 | B2 * | 6/2004 | Beckett | B05C 17/01 222/327 |
| 8,528,785 | B2 * | 9/2013 | Naughton | B05C 17/00553 222/137 |
| 2009/0039113 | A1 | 2/2009 | Hsu | |
| 2016/0327124 | A1 * | 11/2016 | McCloy | F16H 1/2863 |

OTHER PUBLICATIONS

1507 Extended EP Search Report for EP12158727.3, PCT/US2013/029742, Date May 29, 2012, 8pgs.

\* cited by examiner

DISPENSING DEVICE FOR DENTAL MATERIAL

FIELD OF THE INVENTION

The invention relates to a dispensing device for dental material which has at least two plungers for extruding components of the dental material from a container and a planetary gear drive for moving the plungers and the container relative to each other. In the planetary gear drive the annulus gear is radial float-mounted relative to the planet gears. In another aspect the invention relates to the same dispensing device but with the annulus gear being supported against radial inward directed forces only by the planet gears.

BACKGROUND ART

In dentistry a variety of devices are available which allow for preparation and/or application of dental materials in a dentist's practice. In particular for preparation of materials that are typically used at larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M ESPE AG, Germany. Typically such a device allows for two material components to be simultaneously supplied from a package through a mixer where they are mixed. Often the devices provide for continuously extruding the components through a mixer, where the components are mixed as the components flow through the mixer and released from an outlet.

The devices further typically have a motor driven piston for extruding the material from a container. A variety of different drive concepts have been proposed for driving the piston at a relatively high force as it may be required for appropriately dispensing the dental material.

For example EP 1 700 639 discloses a device for dispensing a flowable substance. The device comprises at least one force transmitting member (for example a push-pull chain) adapted to transmit a pushing force in a direction toward or opposite the substance and which can be gathered non-linearly.

Although there are a variety of devices on the market which provide for automatic mixing and dispensing there is still a desire to minimize costs for manufacturing of such devices and for providing the devices with maximized reliability.

SUMMARY OF THE INVENTION

In one aspect the invention relates to a dispensing device for dental material. The device comprises a receptacle for receiving a container for the dental material, at least two plungers for extruding two components of the dental material, for example at least portions of the components, from the container, and a planetary gear drive for moving the plungers and the container relative to each other. The planetary gear drive has at least three planet gears which are in engagement with an annulus gear. The annulus gear is preferably radial float-mounted relative to the planet gears. In particular the annulus gear is supported against radial inward directed forces on the annulus gear only by the planet gears. The planet gears may be supported by the planet gear carrier and/or a sun gear, but preferably there is no additional bearing for supporting the annulus gear relative to the planet gears, the sun gear and/or the planet gear carrier. The device further has a drive shaft, wherein the planetary gear drive is adapted to drive the drive shaft by the planet gear carrier and thereby to move the plungers, and a motor which is engagable with the sun gear for rotating the drive shaft by motor power. In particular the planet gear carrier may be rotationally locked on the drive shaft. Further the device has a second drive shaft for driving a mixing rotor of a dynamic mixer for mixing the components to form the dental material. The second drive shaft may be coupled with the planetary gear drive or may be driven independently.

In a further aspect the invention relates to a planetary gear drive which comprises a drive shaft on which a planet gear carrier is fixed. The planetary gear drive further comprises at least three planet gears which are rotatably suspended on the planet gear carrier and in engagement with an annulus gear. The annulus gear is radial float-mounted relative to the planet gears.

The invention is advantageous in that it allows a relatively simple and compact design of the device. In particular the planetary gear drive may be minimized in complexity and amount of parts used. Further the invention provides for a relatively robust device, for example in operation under harsh surrounding conditions.

In one embodiment the planet gears are rotatably suspended on a planet gear carrier, preferably on one common planet gear carrier suspending all three planet gears. The rotatable suspension of the plant gears and the planet gear carrier may be formed by pins which are fixed on the planet gear carrier and on which the planet gears are arranged by way of a friction or roller bearing.

In a further embodiment the dispensing device, in particular the planetary gear drive, further comprises a sun gear. The sun gear is preferably in engagement with each of the planet gears.

In one embodiment the dispensing device comprises a force transmission member, for example at least one of a chain, one or more gears and a spindle, for moving the plungers. Preferably the planetary gear drive is operable to drive the chain drive via the drive shaft. For example the drive shaft may have one or more sprockets for driving one or more plungers of the device, respectively.

In one embodiment the dispensing device comprises a bearing for radially supporting the planet gear carrier in the dispensing device. The planet gear carrier may be supported relative to the dispensing device by a bearing. For example the drive shaft may be supported relative to the device by a bearing and the planet gear carrier is supported by the drive shaft. In this example the planet gear carrier is indirectly supported relative to the dispensing device by a bearing. In another example the sun gear may be supported by a bearing relative to the device and the sun gear supports the drive shaft. In this example the planet gear carrier is directly supported relative to the dispensing device by a bearing. The skilled person will recognize further possibilities of supporting a part of the planetary gear relative to the device.

Generally at least the drive shaft may be suspended at a fixed position in the device although the drive shaft itself is preferably rotatable relative to the device. Thus a precise movement of the plungers may be ensured.

In one embodiment the device comprises a hand wheel which is engageable with the annulus gear. The hand wheel preferably allows for manually rotating the drive shaft. For example the hand wheel may be coupled with the annulus gear so that the annulus gear can be rotated by rotation of the hand wheel. With the sun gear retained against rotation the rotation of the annulus gear causes the planet gears and thus the planet gear carrier to rotate so that also the drive shaft rotates. Therefore the device preferably allows for manually moving the plungers.

In a further embodiment the motor is engaged with the sun gear via worm gear. Thus in an inactivated stage of the motor the sun gear is automatically blocked against rotation by the worm gear. In that stage a manual movement of the plungers may be enabled.

In one embodiment the dispensing device is adapted to switch the planetary gear drive between a dispensing mode in which the annulus gear is rotationally locked and the sun gear is rotatable relative to the device, and a positioning mode in which the sun gear is rotationally locked and the annulus gear is rotatable relative to the device. The dispensing device may for example have a locking mechanism for rotationally locking the annulus gear in the dispensing mode and unlocking the annulus gear in the positioning mode. Such a locking mechanism may comprise a brake, a ratchet or any other means which allows for the annulus gear to be retained against rotation and selectively for the annulus gear to be released for rotation relative to the device.

In one embodiment the locking mechanism comprises a magnetically driven pawl which is suspended at the device and which is movable relative to a ratchet on the outer circumference of the annulus gear. For locking the annulus gear the pawl may be positioned toward the ratchet so as to provide engagement between the pawl and the ratchet. And for unlocking the annulus gear the pawl may be refracted from the ratchet so as to provide engagement between the pawl and the ratchet. The device may comprise an actuator for controlling the movement of the pawl. Thus a user may operate the actuator for switching between the dispensing and the positioning mode.

In one embodiment at least in the dispensing mode the annulus gear and an imaginary circle on which the planet gears are arranged are in an off-center relationship with each other. Accordingly preferably a play between the annulus gear and each of the planet gears vary as the planetary gear drive operates. Further the play may be generally entirely eliminated between a particular planet gear and the annulus gear at a certain rotational position of the planet gear and the annulus gear relative to each other. In such a rotational position however there is a play between another one of the planet gears and the annulus. Such a varying play between the toothings of the planet gears and the annulus gear may help removing dust and thus may allow for operating the planetary gear drive in harsh surrounding conditions. The off-center relationship may be defined by radial offset between the center axes of the annulus gear and the imaginary circle the planet gears are arranged on. The offset may be between about 0.1 mm and about 1 mm.

In a preferred embodiment the two components are provided in and extruded from at least one container. Such a container may have two compartments for holding the components. Further the two components may be provided in and extruded from two containers each having one compartment for holding one of the components. The skilled person will recognize that likewise such a device may have three or more plungers for extruding three or more components of the dental material. Such a device may use containers having three or more compartments or multiple containers having at least one compartment.

In one embodiment the dispensing device comprises a dynamic mixer for mixing the components. The dynamic mixer is adapted for continuously receiving the components through mixer inlets, for motor driven agitating of the components in a mixing chamber in the mixer through which the components are guided, and for continuously releasing the mixture through a mixer outlet.

In a further embodiment the mixer is preferably removably placeable with the mixer inlets on outlets of the container or compartments. Thus the components extruded from the container or compartments can be extruded into the mixer where the components get mixed before they are released through the mixer outlet.

DETAILED DESCRIPTION OF THE INVENTION

Figure 1:
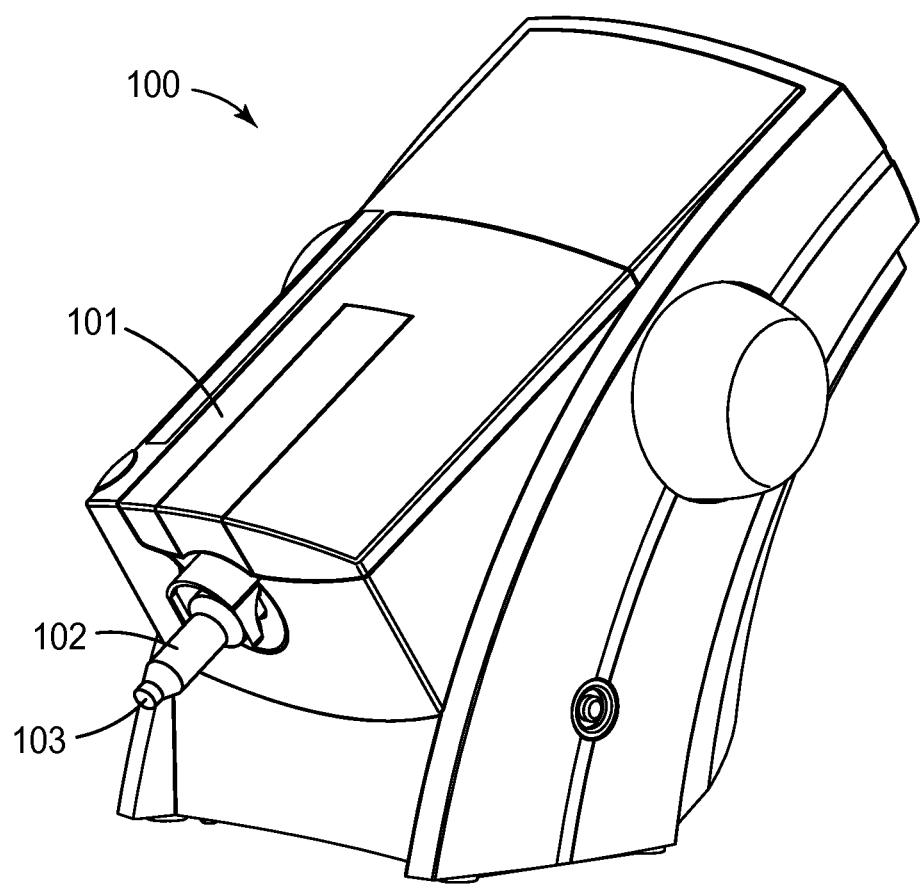
FIG. 1 is a perspective view of a device according to an embodiment of the invention.

FIG. 1 shows a device 100 for dispensing dental materials. The device 100 is adapted for receiving the material, preferably in the form of two separate components, in a receptacle (not visible in this view) of the device 100. The device 100 has further attached thereto a mixer 102 for mixing the components. The material components are preferably contained in separate containers (not shown) from which the components can be extruded into the mixer 102. The mixer 102 is connected with the containers such that the individual components can be advanced into a mixing chamber of the mixer where the components can be mixed, for example by help of a rotating mixing rotor which causes the components to merge to form a mixture. The mixture can exit through an outlet 103 of the mixer 120. The device 100 shown may be used to mix and dispense a hardenable dental impression material, for example. Mixed dental impression material may for example be used to fill a dental tray which is then placed into a patient's mouth for taking a dental impression. The mixer 102 of the device 100 shown is replaceably attached at the device 100. Therefore when the mixed material hardens and thus blocks the mixer the used mixer may be replaced by an unused mixer for the next use of the device 100. A similar device is available under the designation 3M™ ESPE™ Pentamix™ from 3M ESPE AG, Germany.

Figure 2:
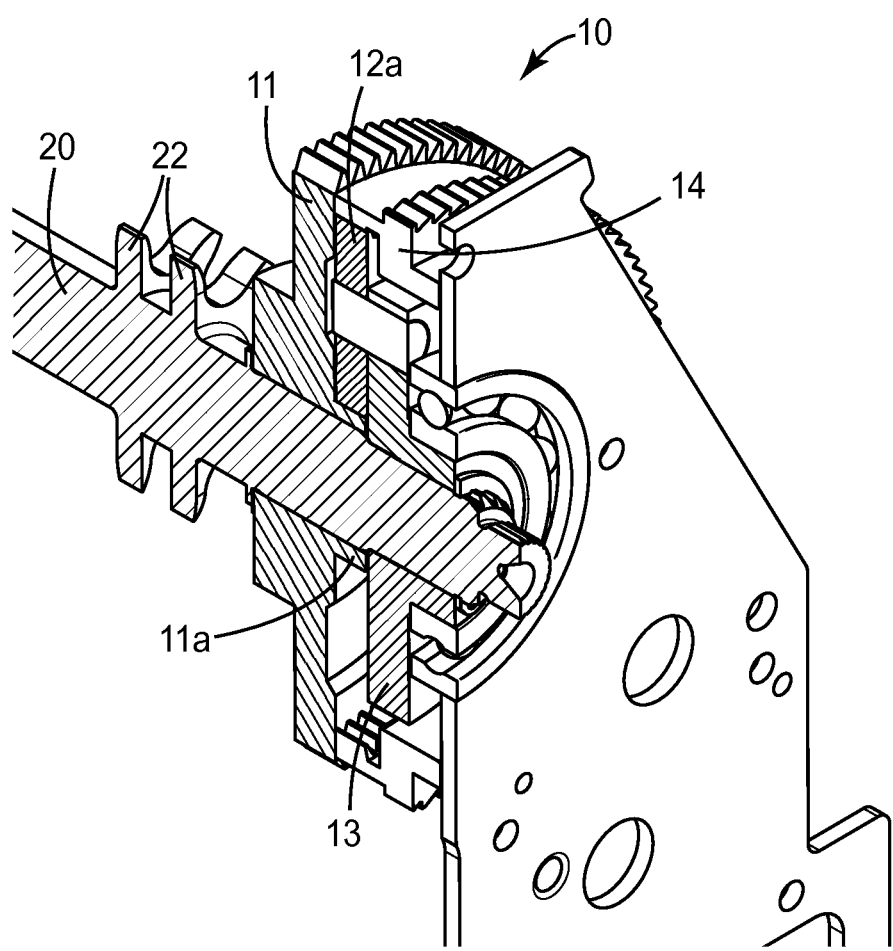
FIG. 2 is a perspective cross-sectional view of a planetary gear drive according to an embodiment of the invention.

FIG. 2 shows a planetary gear drive 10 according to the invention. A sun wheel 11 forms one input of the planetary gear drive 10. The sun wheel 11 accordingly is preferably indirectly or directly coupled to a motor (not shown) of the device (shown in FIG. 1). Further the planetary gear drive 10 has planet gears 12a, 12b, 12c (latter two not visible in this view) which are rotatably arranged on planet gear carrier 13. The planet gears 12a, 12b, 12c and the planet gear carrier 13 together form a planet gear assembly. The planet gear carrier 13 forms an output of the planetary gear drive 10. Therefore the planet carrier 13 is rotationally locked on a drive shaft 20 of the device 10. For example the planet gear carrier 13 may be mounted on the drive shaft 20 via a key joint connection. Alternatively the drive shaft 20 and the planet gear carrier 13 may be formed of a single piece (meaning not assembled from separate pieces), glued or welded onto each other. The skilled person will recognize other solutions for providing the drive shaft 20 and the planet gear carrier 13 to rotationally lock with each other.

In contrast the sun wheel 11 is rotatable relative to the drive shaft 20, in particular the sun wheel 11 is not rotationally locked with the drive shaft 20. The sun wheel 11 may be radially supported on the drive shaft.

For example the sun wheel 11 may be supported by a friction or roller bearing on the drive shaft 20. Thus the sun wheel 11 and the planet gear carrier 13 are adapted to rotate relative to each other. Further the sun wheel 11 and the drive shaft 20 are adapted to rotate relative to each other. The sun wheel 11 has a sun gear 11*a* which is in engagement with the planet gears 12*a*, 12*b*, 12*c*. Accordingly a rotation of the sun wheel 11 causes the planet gears 12*a*, 12*b*, 12*c* to be driven by the sun gear 11*a*.

Further the planetary gear drive 10 has an annulus gear 14 which forms an alternative input of the planetary gear drive 14. The annulus gear 14 is also in engagement with each of the planetary gears 12*a*, 12*b*, 12*c*. Therefore the sun gear 11*a*, each of the planet gears 12*a*, 12*b*, 12*c* and the annulus gear 14 are in geared connection with each other. Accordingly a rotation of the sun gear 11*a* and the annulus gear 14 relative to each other causes the planet gears 12*a*, 12*b*, 12*c* to rotate and thereby to circulate relative to the sun gear 11*a* and/or the annulus gear 14. The circulation of the planet gears 12*a*, 12*b*, 12*c* causes the planet gear carrier 13 and thus the drive shaft 20 to rotate.

According to the invention the annulus gear 14 is radial float-mounted relative to the planet gear assembly and thus also relative to the drive shaft 20. In particular the annulus gear 14 is radially supported relative to the drive shaft 20 only by the planet gear assembly (by the planet gear carrier 13 with the planet gears 12*a*, 12*b*, 12*c*). Further a play between the planet gears 12*a*, 12*b*, 12*c* and the annulus gear 14 provides for the annulus gear 14 to be radially floatable relative to the drive shaft 20 and/or the planet gear assembly. This is in contrast to the prior art according to which the annulus gear and the planet gear carrier and/or the drive shaft are coaxially guided relative to each other so as provide proper operation of the planetary gear drive over longer time periods. It has however been found that the invention allows a planetary gear drive to be provided with a sufficient life time, particularly if lubricated for life or if dry running. Further a planetary gear drive according to the invention was found to be relatively robust if operated in harsh ambient conditions.

The drive shaft 20 has one or more sprockets 22 for driving a chain for each plunger of the device. Preferably a push-pull chain is used with the device of the invention. Such a push-pull chain is adapted such that folding of an elongated portion of the chain is permitted only in one direction of a dimension laterally to a further dimension along which the chain extends. Further the push-pull chain is adapted such that the elongated portion of the chain is self-maintaining elongated when exposed to a pushing force in the dimension in which the chain extends. Thus the same portion of a push-pull chain allows for transmission of a pushing force (ends of elongated portion urged toward each other) and pulling force (ends of elongated portion urged away from each other) and for being folded. The skilled person will however recognize that the drive shaft may be used to drive one or more standard pull chains, or one or more spindles for moving the plungers.

Figure 3:
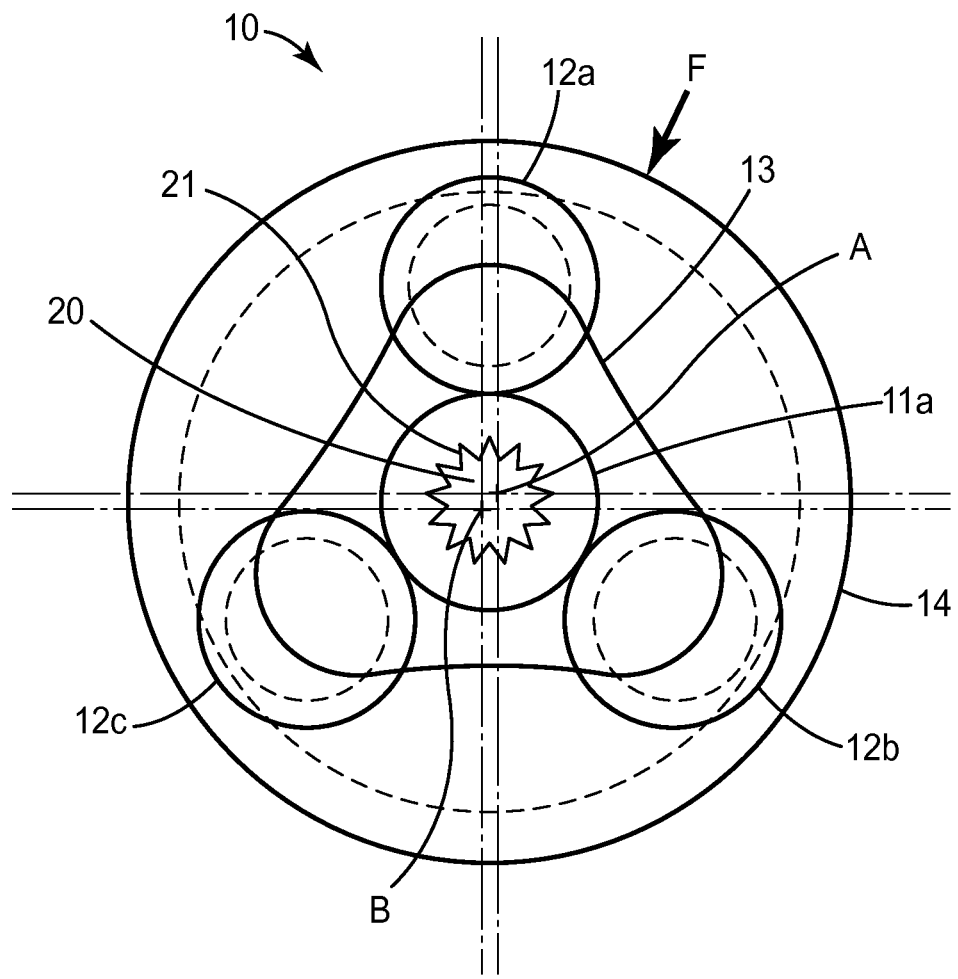
FIG. 3 is a schematic view of the planetary gear drive shown in FIG. 2.

FIG. 3. illustrates the planetary gear drive 10 in a schematic front view. The planetary gear drive 10 has a center axis A which preferably corresponds to a rotation axis of the drive shaft 20. The planet carrier 13 is mounted on the drive shaft 20 by keyed connection 21. Thereby the planet carrier 13 and the drive shaft 20 are anti-twist locked with each other. Further the planet carrier 13 carries the planet gears 12*a*, 12*b* and 12*c*. The planet gears 12*a*, 12*b* and 12*c* have a generally equal diameter and are rotatably arranged on the planet carrier 13 at a generally equal distance relative to the center axis A. Each of the planet gears 12*a*, 12*b*, 12*c* further are in engagement with the sun gear 11*a* as well as with the annulus gear 14. Therefore the planet gears 12*a*, 12*b*, 12*c* establish a geared connection between the sun gear 11*a* and the annulus gear 14. In operation either the sun gear 11*a* or, alternatively, the annulus gear 14 may be used as input to drive the drive shaft 20. Thereby each of the planet gears 12*a*, 12*b*, 12*c* are rotated and thus caused to move on an imaginary circle about the center axis A. Such circular movement of the planet gears 12*a*, 12*b*, 12*c* causes the planet carrier 13 and thereby the drive shaft 20 to move.

Preferably the device is adapted to switch the planetary gear drive between a dispensing mode, in which the piston(s) can be moved at relatively high forces for dispensing dental material from the device, and a positioning mode in which the pistons are movable at desired positions relatively rapidly.

In the dispensing mode preferably the annulus gear 14 is locked relative to the device and the sun gear 11*a* (via the sun wheel which is not visible in this view) is used as input, for example rotated relative to the device by a motor. Alternatively, in the positioning mode the sun wheel with sun gear 11*a* are locked relative to the device and the annulus gear 14 is used as input, for example rotated by hand. Accordingly based on the same rotation speed at the different inputs the planetary gear drive provides for a first rotation speed of the drive shaft 20 in the dispensing mode and for a different second rotation speed of the drive shaft 20 in the positioning mode. Preferably the first rotation speed is lower than the second rotation speed. The annulus gear 14 may for example be coupled to a hand wheel for manually driving the drive shaft 20 via the planetary gear drive 10 in the positioning mode, whereas the motor may drive the drive shaft 20 in the dispensing mode. The skilled person will recognize that the positioning mode is optional although it may provide certain advantages. For example the positioning mode may allow the pistons to be retracted rapidly for exchanging the container for the dental material, and to reposition the pistons likewise rapidly toward another container replaced into the device.

In the example the annulus gear is radially urged toward the center axis A by a radial force F. Such a radial force may result from locking the annulus gear 14 relative to the device for activation of the dispensing mode. Due to the annulus gear 14 being radial float-mount relative to the planet gear carrier 13 the annulus gear 14 therefore is urged into an off-center relationship relative to the center axis A. Accordingly a center axis B of the annulus gear 14 is generally parallel offset from the center axis A of the planetary gear drive 10.

In operation of the planetary gear drive 10 in the dispensing mode each of the rotation axes of the planet gears 12*a*, 12*b*, 12*c* vary in distance relative the annulus gear 14 as the planet carrier 13 and the annulus gear 14 rotate relative to each other. Therefore the contact areas between the teeth of the planet gears 12*a*, 12*b*, 12*c* and the annulus gear 14 vary. Thus a self-cleaning effect of the gear toothing may be provided and wear of the gears may be minimized.

The invention claimed is:

1. A radial gear drive, comprising:
   a planetary gear drive comprising a planet gear assembly comprising at least three planet gears rotatably suspended on a planet gear carrier such that the at least three planet gears each respectively rotate about their center axis; wherein the center axes of the at least three planet gears are arranged about an imaginary circle defined by rotation of the planet gear carrier about its center axis such that the center axes of the at least three planet gears travel along the imaginary circle when the planet gear carrier rotates; wherein each of the at least three planet gears in the planet gear assembly is in engagement with an annulus gear;

wherein the planet gear carrier is rotationally locked on a drive shaft such that rotation of the annulus gear drives the at least three planet gears in the planetary gear drive and drives the drive shaft, and wherein the annulus gear is radially floatable relative to the drive shaft and the planet gear assembly, and wherein a radial force applied on the annulus gear urges the annulus gear into an off-center relationship with respect to the imaginary circle on which the at least three planet gears are arranged.

2. The radial gear drive of claim 1, further comprising a sun gear engaged with each of the at least three planet gears.

3. The radial gear drive of claim 1, wherein the off-center relationship is defined by radial offset between a center axis of the annulus gear and a center axis of the imaginary circle of between about 0.1 mm and about 1 mm.

\* \* \* \* \*

UNITED STATES PATENT AND TRADEMARK OFFICE
CERTIFICATE OF CORRECTION

PATENT NO. : 9,795,985 B2
APPLICATION NO. : 14/379959
DATED : October 24, 2017
INVENTOR(S) : Emir Jelovac Page 1 of 1

It is certified that error appears in the above-identified patent and that said Letters Patent is hereby corrected as shown below:

In the Specification

Column 2
Line 6, delete "engagable" and insert -- engageable --, therefor.

Column 2
Lines 58-61, delete "Generally at least the drive shaft may be suspended at a fixed position in the device although the drive shaft itself is preferably rotatable relative to the device. Thus a precise movement of the plungers may be ensured." and insert the same on Column 2, Line 57, as a continuation of the same paragraph.

Column 3
Line 29, delete "refracted" and insert -- retracted --, therefor.

Signed and Sealed this
Fifth Day of June, 2018

Andrei Iancu
*Director of the United States Patent and Trademark Office*